US00PP13181P2

(12) United States Plant Patent
Brown

(10) Patent No.: US PP13,181 P2
(45) Date of Patent: Nov. 5, 2002

(54) SUTERA PLANT NAMED 'BACOBLE'

(75) Inventor: Graham Brown, Baulkham Hills (AU)

(73) Assignee: Nuflora International Pty. Ltd., Sydney (AU)

( * ) Notice: Subject to any disclaimer, the term of this patent is extended or adjusted under 35 U.S.C. 154(b) by 0 days.

(21) Appl. No.: 09/996,373

(22) Filed: Nov. 30, 2001

(51) Int. Cl.[7] ..... A01H 5/00
(52) U.S. Cl. ..... Plt./263
(58) Field of Search ..... Plt./263

(56) References Cited

PUBLICATIONS

UPOV ROM GTITM Computer Database 2001/06, GTI JOUVE Retrival software, citations for 'Bacoble'.*

* cited by examiner

*Primary Examiner*—Bruce R. Campell
*Assistant Examiner*—W C Baker
(74) *Attorney, Agent, or Firm*—C. A. Whealy

(57) ABSTRACT

A new and distinct cultivar of Sutera plant named 'Bacoble', characterized by its mounded, low spreading and cascading plant habit; freely and continuous branching habit; and numerous salverform flowers that are violet blue in color.

1 Drawing Sheet

BOTANICLA CLASSIFICATION/CULTIVAR DESIGNATON

*Sutera cordata* cultivar Bacoble.

BACKGROUND OF THE INVENTION

The present Invention relates to a new and distinct cultivar of Sutera plant, botanically known as *Sutera cordata*, and hereinafter referred to by the cultivar name Bacoble.

The new Sutera is a product of a planned breeding program conducted by the Inventor in Cobbitty, New South Wales, Australia. The objective of the breeding program is to create new Suteras with numerous violet blue-colored flowers.

The new Sutera originated from a cross made by the Inventor in 1998 of a proprietary Sutera selection identified as X96.3.1, not patented, as the female, or seed parent, with a proprietary Sutera selection identified as X96.3.2, not patented, as the male, or pollen parent. The new Sutera was selected as a single plant from the resulting progeny by the Inventor in 1998, in Cobbitty, New South Wales, Australia, on the basis of its numerous violet blue-colored flowers.

Asexual reproduction of the new cultivar by terminal cuttings taken in Cobbitty, New South Wales, Australia since 1998 has shown that the unique features of this new Sutera are stable and reproduced true to type in successive generations.

SUMMARY OF THE INVENTION

Plants of the cultivar Bacoble have not been observed under all possible environmental conditions. The phenotype may vary somewhat with variations in environment such as temperature, light intensity and daylength without, however, any variance in genotype.

The following traits have been repeatedly observed and are determined to be the unique characteristics of 'Bacoble'. These characteristics in combination distinguish 'Bacoble' as a new and distinct cultivar:

1. Mounded, low spreading and cascading plant habit.
2. Freely and continuous branching.

3. Numerous salverform flowers that are violet blue in color.

Plants of the new Sutera differ primarily from plants of the parent selections in flower color as plants of the new Sutera have much darker violet blue-colored flowers than plants of either parent selection.

Plants of the new Sutera can be compared to plants of the Sutera cultivar Lavender Showers, disclosed in U.S. Plant patent application Ser. No. 09/450,098. In side-by-side comparisons conducted in Cobbitty, New South Wales, Australia, plants of the new Sutera differed from plants of the cultivar Lavender Showers primarily in flower color as plants of the new Sutera have darker violet blue-colored flowers.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs may differ slightly from the color values cited in the detailed botanical description which accurately describe the colors of the new Sutera.

The photograph at the top of the sheet comprises a side perspective view of three typical flowering plants of 'Bacoble' grown in a 21.5-cm container.

The photograph at the bottom of the sheet comprises a close-up view of a typical leaves and flowering stems of 'Bacoble'.

DETAILED BOTANICAL DESCRIPTION

The aforementioned photographs and following observations and measurements describe plants grown in Encinitas, Calif., in an outdoor nursery under full sunlight conditions during the late winter and early spring with day temperatures averaging 18° C. and night temperatures averaging 13° C. Plants were grown for 18 weeks in 21.5-cm containers with three plants per container and were pinched one time. Color references are made to The Royal Horticultural Society Colour Chart, version 1995, except where general terms of ordinary dictionary significance are used.

Botanical classification: *Sutera cordata* cultivar Bacoble.

Parentage:

*Female parent.*—Proprietary *Sutera cordata* selection identified as X96.3.1, not patented.

*Male parent.*—Proprietary *Sutera cordata* selection identified as X96.3.2, not patented.

Propagation:

*Type cutting.*—Terminal vegetative cuttings.

*Time to initiate roots.*—Summer: About 8 days at 28° C. Winter: About 12 days at 15° C.

*Time to develop roots.*—Summer: About 21 days at 28° C. Winter: About 28 days at 15° C.

*Root description.*—Fine and fibrous.

*Rooting habit.*—Freely branching.

Plant description:

*Form.*—Initially upright, then low spreading and cascading; uniform; plants eventually becoming hemispherical to spherical in shape. Freely branching with lateral branches potentially forming at every node. Vigorous growth habit.

*Plant height.*—About 8 cm.

*Plant diameter.*—About 36 cm.

*Lateral branches.*—Length: About 40 cm. Diameter: About 1.5 mm. Internode length, mature: About 3 cm. Texture: Pubescent; tiny white hairs. Color: Mature: More gray than 187A. Young: 144B.

*Foliage description.*—Arrangement: Opposite; simple. Quantity per lateral branch: About 22. Length: About 1.7 cm. Width: About 1.2 cm. Shape: Ovate. Apex: Broadly acute. Base: Obtuse. Margin: Serrate. Texture: Upper surface: Smooth, glabrous. Lower surface: Pubescent. Venation pattern: Pinnate. Fragrance: Spicy. Color: Young foliage, upper surface: 144A. Young foliage, lower surface: 144B. Mature foliage, upper surface: 137A. Mature foliage, lower surface: 137C. Venation, upper surface: 137A. Venation, lower surface: 137C. Petiole length: About 3 mm. Petiole diameter: About 1 mm. Petiole color: 147B.

Flower description:

*Flower type and habit.*—Solitary axillary flowers; salverform; slender corolla tubes flare abruptly into five rounded lobes. Flowers persistent. Very freely flowering; typically two flowers per node and about 25 buds and flowers per lateral branch over the production time of the plant. Flowers face mostly upward or outward.

*Natural flowering season.*—Plants typically flower from spring until fall; flowering continuous during this period.

*Flower longevity on the plant.*—About 3 to 4 days.

*Fragrance.*—Not detected.

*Flower size.*—Diameter: About 1.3 cm. Tube length: About 8 mm. Throat diameter, distal end: About 3 mm. Tube diameter, proximal end: About 2.5 mm.

*Flower buds* (*showing color*).—Length: About 6 mm. Diameter: About 2 mm. Shape: Obovate. Color: 92B.

*Corolla.*—Quantity/arrangement: Five fused petals; slender corolla. tube flaring abruptly into five rounded lobes. Petal lobe length from throat: About 5 mm. Petal lobe width: About 3 mm. Petal lobe shape: Roughly spatulate. Petal lobe apex: Rounded. Petal lobe margin: Entire. Texture: Smooth, velvety. Color: Petal lobe, upper surface, when opening: 92A. Petal lobe, lower surface, when opening; 92B. Petal lobe, upper surface, fully opened: 92B; color fading to 92C to 92D with subsequent development. Petal lobe, lower surface, fully opened: 92C. Flower throat (inside): 17A. Flower tube (outside): Towards apex, 92C; towards base, 8C.

*Sepals.*—Arrangement/appearance: Single whorl of five sepals fused at base; shallow cup-shaped calyx. Calyx length: About 5 mm. Calyx diameter: About 2.5 mm. Shape: Narrow, linear. Apex: Narrowly acute. Margin: Entire. Texture, upper and lower surfaces: Slightly pubescent. Color: Upper surface: 144B. Lower surface: 144A.

*Peduncles.*—Length: About 7 mm. Width: Less than 1 mm. Angle: About 45° from the stem. Strength: Strong; slender. Texture: Smooth. Color: 144A.

*Reproductive organs.*—Stamens: Quantity per flower: Five. Anther shape: Reniform. Anther length: Less than 1 mm. Anther color: 12A. Pollen amount: Scarce. Pollen color: 12A. Pistils: Quantity per flower: One. Pistil length: About 1 cm. Style length: About 9 mm. Style color: 151D. Stigma shape: Club-shaped. Stigma color: 151A. Ovary color: 144C.

*Seed/fruit.*—Seed nor fruit production has not been observed.

Disease/pest resistance: Plants of the new Sutera have not been noted to be resistant to pathogens or pests common to Sutera.

Tempeature tolerance: Plants of the new Sutera have been observed to tolerate temperatures from 4 to 33° C.

It is claimed:

1. A new and distinct cultivar of Sutera plant named 'Bacoble', as illustrated and described.

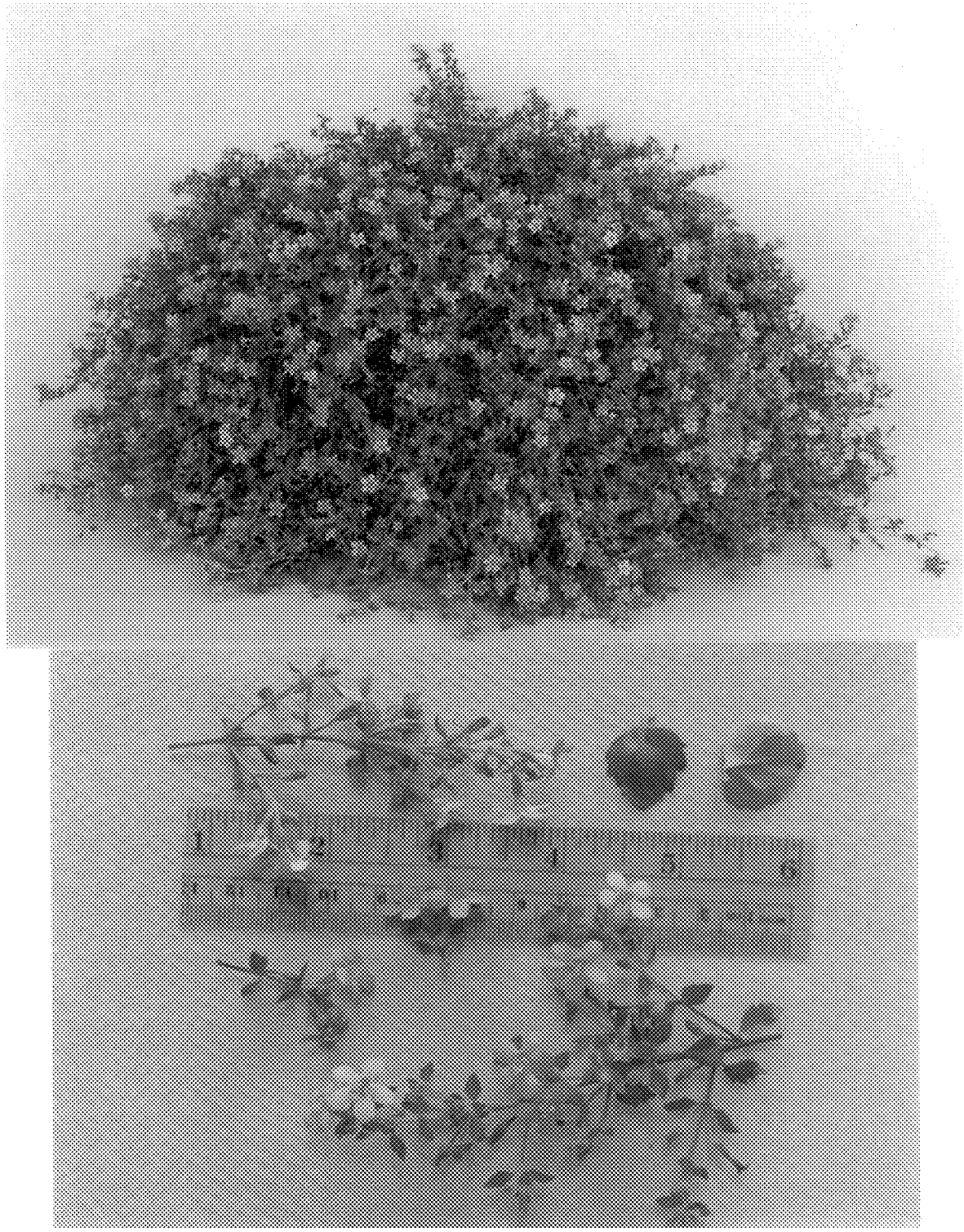

* * * * *